United States Patent [19]

Schroeder et al.

[11] Patent Number: 5,362,908
[45] Date of Patent: Nov. 8, 1994

[54] CATALYST AND METHOD FOR PURIFYING CRUDE TEREPHTHALIC ACID, ISOPHTHALIC ACID OR NAPHTHALENE DICARBOXYLIC ACID

[75] Inventors: Hobe Schroeder, Naperville; Ricky L. Wittman, Aurora, both of Ill.

[73] Assignee: Amoco Corporation, Chicago, Ill.

[21] Appl. No.: 29,037

[22] Filed: Mar. 10, 1993

[51] Int. Cl.$^5$ .................. C07C 51/42; C07C 51/487
[52] U.S. Cl. .................. 562/487; 562/412; 562/485
[58] Field of Search ............ 562/487, 485, 412

[56] References Cited

U.S. PATENT DOCUMENTS

| | | | |
|---|---|---|---|
| 3,584,039 | 6/1971 | Meyer | 260/525 |
| 4,743,577 | 5/1988 | Schroeder et al. | 502/326 |
| 4,831,008 | 5/1989 | Timmer et al. | 502/328 |

OTHER PUBLICATIONS

M. Bankmann et al., "Forming of High Surface Area TiO$_2$ To Catalyst Supports", Symposium on Catalyst Supports: Chemistry, Forming and Characterization, presented before the Division of Petroleum Chemistry, Inc., American Chemical Society, New York City Meeting, Aug. 25-30, 1991.

M. Bankmann et al., "Forming of High Surface Area TiO$_2$ To Catalyst Supports", *Catalysis Today*, vol. 14, pp. 225–242 (1992).

*Primary Examiner*—Jose G. Dees
*Assistant Examiner*—Barbara Frazier
*Attorney, Agent, or Firm*—James R. Henes; Wallace L. Oliver

[57] ABSTRACT

A method is disclosed for the purification of crude terephthalic acid, crude isophthalic acid or a crude naphthalene dicarboxylic acid that employs a titanium dioxide-supported purification catalyst.

14 Claims, No Drawings

CATALYST AND METHOD FOR PURIFYING CRUDE TEREPHTHALIC ACID, ISOPHTHALIC ACID OR NAPHTHALENE DICARBOXYLIC ACID

BACKGROUND OF THE INVENTION

1. Field of the Invention

This invention relates generally to a catalyst and method employing such catalyst for purifying crude terephthalic acid, crude isophthalic acid or a crude naphthalene dicarboxylic acid, and more particularly concerns the use in the aforesaid purification method of a catalyst comprising at least one metal of Group VIII of the Periodic Table supported on a carrier comprising titanium dioxide.

2. Discussion of the Prior Art

Polymer grade or "purified" terephthalic acid and isophthalic acid are the staring materials for polyethylene terephthalates and isophthalates, respectively, which are the principal polymers employed in the manufacture of polyester fibers, polyester films, and resins for bottles and like containers. Similarly, polymer grade or "purified" naphthalene dicarboxylic acids, especially 2,6-naphthalene dicarboxylic acid, are the starting materials for polyethylene naphthalates, which can also be employed in the manufacture of fibers, films and resins. A purified terephthalic acid, isophthalic acid or naphthalene dicarboxylic acid can be derived from a relatively less pure, technical grade or "crude" terephthalic acid, isophthalic acid or "crude" naphthalene dicarboxylic acid, respectively, by purification of the crude acid utilizing hydrogen and a noble metal catalyst, as described for terephthalic acid in U.S. Pat. No. 3,584,039 to Meyer. In the purification process, the impure terephthalic acid, isophthalic acid or naphthalene dicarboxylic acid is dissolved in water or other suitable solvent or solvent mixture at an elevated temperature, and the resulting solution is hydrogenated, preferably in the presence of a hydrogenation catalyst, which conventionally is palladium on a carbon support, as described in Pohlmann, U.S. Pat. No. 3,726,915. This hydrogenation step converts the various color bodies present in the relatively impure phthalic acid or naphthalene dicarboxylic acid to colorless products. Another related purification-by-hydrogenation process for aromatic polycarboxylic acids produced by liquid phase catalyst oxidation of polyalkyl aromatic hyrdocarbons is described in Stech et al., U.S. Pat. No. 4,405,809.

Carbon is conventionally used as the support material for the noble metal in the catalyst employed in the aforesaid purification method. A common disadvantage of the use of a carbon support is that carbon fines are often generated during commercial operations. The generation of such fines can be minimized but generally cannot be completely avoided. During the subsequent esterification process, such particulates introduced with the particular purified acid, for example, terephthalic acid, isophthalic acid or 2,6-naphthalene dicarboxylic acid, can plug filters and thereby cause interruptions in the process. Other such particulates that bypass the filter may be incorporated into the resulting polyester fiber or film and cause fiber breakage or film distortion.

For this reason, it is highly desirable to use other materials as the support material in the catalyst employed in the aforesaid purification method. However, because of the highly corrosive conditions under which the aforesaid purification is performed, it has proven difficult to develop suitable non-carbon catalyst supports for use in the purification catalyst. For example, as indicated in Meyer, U.S. Pat. No. 3,584,039 in column 5, lines 10–14, hot aqueous solutions of terephthalic acid dissolve supporting materials such as natural and synthetic alumina, silica, silica-alumina, kieselguhr, calcined clays, zirconium supports and other metal oxides and metal salt containing supports.

M. Bankmann, R. Brand, B. H. Engler and J. Ohmer, "Forming of High Surface Area $TiO_2$ to Catalyst Supports," *Catalysis Today*, Vol. 14, pages 225–242 (1992), contains an extensive discussion of the use of titanium dioxide having a high surface area as a catalyst support. The article (which was previously presented in a substantially identical form by R. Brand at the Fall, 1991, American Chemical Society meeting) indicates that the titanium dioxide must have a high surface area in order to be a suitable catalyst support and discusses only titanium dioxide having surface areas of 50 and 100 square meters per gram. The article discusses the extrusion process for manufacturing titanium dioxide having the requisite high surface area and the effect of the raw materials, additives and process parameters employed in the extrusion process on catalytically important characteristics of the resulting titanium dioxide. As disclosed, the extrusion process involves the steps of (1) mixing and kneading the raw materials, (2) extruding, (3) drying, and (4) calcining, each of which influences the quality of the resulting support. Correlations between the concentration of water, plasticizers and binders and the type of titanium dioxide raw material employed in the mixing and kneading step and the crushing strength, attrition resistance, pore diameter and pore volume of the resulting catalyst support, and correlations between the calcination temperature and the surface area, pore volume, mean pore diameter and pore size distribution and the degree of transformation from the anatase crystalline phase to the rutlie crystalline phase in the resulting catalyst support, are discussed in the article. More particularly, the use of catalysts containing palladium, platinum or rhodium components supported on titanium dioxide for selective hydrogenation is discussed. On pages 240–241, the use of such catalysts to hydrogenate a para-substituted benzaldyhyde to the corresponding para-substituted benzyl alcohol or para-substituted toluene is disclosed. The table on page 241 indicates that the para-substituent can be a carboxylic acid group, a methyl group or a halogen. The article discloses that the results of the hydrogenation of para-substituted benzaldyhyde were substantially different depending upon whether the catalyst contained palladium, platinum or rhodium on the titanium dioxide support. The article indicates that the titanium dioxide must have a high surface area in order to be a suitable catalyst support and discusses only titanium dioxide having surface areas of 50 and 100 square meters per gram. In addition, the article discloses that depending on the reaction temperature employed, the reduction of a parasubstituted benzaldehyde affords either of several products with high selectivity and in high yield. Except for the catalyst, the reaction temperature and the hydrogen pressure employed, the article does not disclose the conditions under which the hydrogenation was performed.

Schroeder et al., U.S. Pat. No. 4,743,577, discloses that the use of catalysts containing palladium finely dispersed on carbon in the aforesaid purification of terephthalic acid derived from the oxidation of p-xylene results in contamination of the resulting purified terephthalic acid with fines produced by abrasion of the carbon granulates due to their relatively low crush strength and abrasion resistance. This patent discloses that reduced fines contamination results from the use instead of a catalyst containing a thin layer of palladium, nickel, rhodium, platinum, copper, rhuthenium and cobalt on a porous sintered support of metallic titanium, zirconlure, tungsten, chromium, nickel and alloys incorporating one or more of these metals. The surface area of palladium-plated supports of titanium, incoriel and nickel are disclosed as 0.22, 0.55 and 1.21 square meters per gram, respectively, which are very significantly smaller than specific surface area of a palladium on active carbon catalyst.

Sikkenga et al., pending U.S. patent application Ser. No. 07/900,593, filed Jun. 18, 1992, discloses the preparation of an aromatic carboxylic acid by the liquid phase catalyzed oxidation of an alkyl-substituted aromatic compound such as o-, m-, or p-xylene or 2,6-dimethylnaphthalene. The application further discloses on page 11, lines 23-31, that the resulting aromatic carboxylic acids can be purified by hydrogenation thereof in the presence of a catalyst comprising one or more Group VIII metals deposited on a support such as alumina, titania or carbon. The application contains no other mention of titania.

Holzhauer et al., pending U.S. patent application Ser. No. 07/900,637, filed Jun. 18, 1992, discloses on page 27, lines 1-12, a method for purifying 2,6-naphthalene dicarboxylic acid by treating it with hydrogen in the presence of a hydrogenation catalyst containing one or more of platinum, palladium, rhodium, ruthenium, osmium and iridium supported on alumina, silica-alumina, silica, titania, clays and zirconia. The application contains no other mention of titania.

Timruer et al., U.S. Pat. No. 4,831,008, discloses the use of a catalyst containing a rhodium-containing component supported on titanium dioxide for the hydrogenation of benzene, toluene, o-xylene, terephthalic acid, disodium terephthalate, and diethyl terephthalate, in which the aromatic ring is hydrogenated.

OBJECTS OF THE INVENTION

It is therefore a general object of the present invention to provide an improved method which overcomes the aforesaid problems of prior art methods, for purifying a crude phthalic acid or crude naphthalene dicarboxylic acid produced by the liquid-phase oxidation of o-, m-, or p-xylene or a dialkylnaphthalene, respectively, with an oxygen-containing gas in a solvent and in the presence of an oxidation catalyst.

More particularly, it is an object of the present invention to provide an improved aforesaid purification method that employs a catalyst which does not produce particulates during the purification operation and yet has a high catalytic activity and lifetime.

It is another object of the present invention to provide an improved aforesaid purification method that employs a catalyst that, even after a substantial period of aging, reduces the amounts of 4-carboxybenzaldehyde and 4-hydroxymethylbenzoic acid to substantially lower levels.

Other objects and advantages of the invention will become apparent upon reading the following detailed description and appended claims.

SUMMARY OF THE INVENTION

These objects are achieved by the method of this invention for the purification of crude terephthalic acid, isophthalic acid or crude naphthalene dicarboxylic acid produced in the liquid-phase oxidation of benzene having two oxidizable alkyl or acyl ring substituents or an oxidizable alkyl and acyl ring substituent in the meta or para positions or naphthalene having two oxidizable alkyl or acyl ring substituents or an oxidizable alkyl and acyl ring substituent, with an oxygen-containing gas in a solvent at an elevated temperature and pressure and in the presence of an oxidation catalyst comprising a heavy metal, wherein the purification comprises passing an at least partially aqueous solution of from about 5 to about 50 weight percent of the crude terephthalic acid, isophthalic acid or crude naphthalene dicarboxylic acid, at a temperature of from about 100° C. to about 350° C. and at a pressure sufficient to maintain the solution substantially in the liquid phase, through a particulate catalyst bed and in the presence of hydrogen, wherein the particulate catalyst comprises a noble metal of Group VIII of the Periodic Table of Elements on a titanium dioxide support, which does not disintegrate in less than one month under the aforesaid conditions employed in the purification. This invention is also the composition of the catalyst employed in the method of this invention.

DETAILED DESCRIPTION OF THE PREFERRED EMBODIMENTS

The method of this invention is suitable for use in the purification of a crude terephthalic acid, isophthalic acid or a crude naphthalene dicarboxylic acid prepared by the catalytic, liquid-phase oxidation of benzene having two oxidizable alkyl or acyl ring substituents or an oxidizable alkyl and acyl ring substituent in the meta or para positions or naphthalene having two oxidizable alkyl or acyl ring substituents or an oxidizable alkyl and acyl ring substituent in a solvent. Suitable alkyl groups contain from 1 to 6 carbon atoms, and suitable acyls also contain from 1 to 6 carbon atoms. Examples of suitable naphthalene-based aromatic feed compounds include: 1,2-dimethylnaphthalene, 2,6-dialkylnaphthalene or 2-acyl-6-alkylnaphthalene, 2,6-dimethyl-, 2,6-diethyl- or 2,6-diisopropyl-, 2-acetyl-6-methyl- and 2-methyl-6-ethylnaphthalene. The crude acid being purified preferably is either terephthalic acid formed by the oxidation of p-xylene, isophthalic acid formed by the oxidation of m-xylene or 2,6-naphthalene dicarboxylic acid formed by the oxidation of 2,6-dialkylnaphthalene (preferably 2,6-dimethylnaphthalene), and more preferably is terephthalic acid formed by the oxidation of p-xylene. It is of course understood that, prior to being purified, the crude acid, for example, 2,6-naphthalene dicarboxylic acid, can have been previously esterified to form the ester, for example, dimethyl naphthalene dicarboxylate, and then hydrolized to form the acid which is then purified by the method of this invention.

Suitable solvents for use in the oxidation step of the method for producing the crude acid to be purified by the method of this invention include water and any aliphatic $C_2$-$C_6$ monocarboxylic acid such as acetic acid, propionic acid, n-butyric acid, isobutyric acid, n-valeric acid, trimethylacetic acid and caproic acid, and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude acid product from the product stream, at least a portion of the mother liquor (solvent) in the resulting product stream is generally recycled to the reactor.

The source of molecular oxygen employed in the oxidation step of the aforesaid method for producing the crude phthalic acid or crude naphthalene dicarboxylic acid product to be purified by the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl substituent of the m- or p-xylene or dimethylnaphthalene being oxidized will provide such 0.5 to 8 volume percent of oxygen (measured on a solvent-free basis) in the gas-vapor mixture in the condenser.

The catalyst employed in the aforesaid oxidation method for producing the crude terephthalic or isophthalic acid or crude naphthalene dicarboxylic acid product comprises a heavy metal component, and can additionally comprise promoters or accelerators known in the art. In general, suitable heavy metal oxidation catalysts include those metals having an atomic number of about 21 to about 82, inclusive. A promoter such as a suitable source of bromide, a low molecular weight ketone having from 2 to 6 carbon atoms or a low molecular weight aldehyde having 1 to 6 carbon atoms can be used. The catalyst preferably comprises cobalt, more preferably comprises cobalt, and manganese-containing components, and most preferably comprises cobalt, manganese, and bromine-containing components. The weight ratio of cobalt (calculated as elemental cobalt) in the cobalt component of the catalyst-to- p- or m-xylene, or -to-dialkyl, -diacyl or -acylalkylnaphthalene in the liquid-phase oxidation is in the range of from about 0.2 to about 30 milligram atoms (mga) per gram mole of the m- or p-xylene or dialkyl naphthalene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 30 mga per toga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per toga of total cobalt and manganese.

Each of the cobalt and manganese components can be provided in any of its known ionic or combined forms that provide reactive forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-dibromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

In operation, the minimum pressure at which the oxidation reactor is maintained is that pressure which will maintain a substantial liquid phase of the m- or p-xylene and at least 70 percent of the solvent. The m- or p-xylene or dialkylnaphthalene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

The oxidation can be performed either in a batch, continuous, or semicontinuous mode. In the batch mode, the aforesaid substituted benzene or naphthalene to be oxidized, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the aforesaid substituted benzene or naphthalene to be oxidized has been completely introduced into the reactor, the temperature of the reactor contents is raised. In the continuous mode, each of the aforesaid substituted benzene or naphthalene to be oxidized, air, solvent, and catalyst are continuously introduced into the oxidation reactor, and a product stream comprising the resulting crude acid oxidation product and catalyst components dissolved in the solvent is withdrawn from the reactor. In the semicontinuous mode, the solvent and catalyst are initially introduced into the reactor and then the aforesaid substituted benzene or naphthalene to be oxidized and air are continuously introduced into the reactor.

For large-scale commercial operation, it is preferable to use a continuous oxidation process. In such a process, the weight ratio of monocarboxylic acid solvent to the aromatic feed to be oxidized is preferably about 2:1 to about 12:1, the toga ratio of manganese to cobalt is about 15:1 to about 0.3:1, the toga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 185° C. to about 250° C. Acetic acid is the most suitable solvent for such preferred continuous oxidation.

Depending on the oxidation reaction conditions used, the aromatic feed compound selected, the oxidation catalysts, and the levels of catalyst selected, the reaction mixture produced in the oxidation reaction contains, in addition to the desired aromatic carboxylic acid, a number of impurities and reaction by-products. For example, terephthalic acid impurities are of several types. The compound 4-carboxybenzaldehyde (4-CBA), an intermediate product in the oxidation of para-xylene, is found in impure terephthalic acid. Unidentified color-forming precursors and color bodies, possibly of the benzil, fluorenone or anthraquinone structure, are also usually present. Nitro-compounds are found as impurities in terephthalic acid obtained by liquid phase nitric acid oxidation of para-xylene and other suitable starting materials.

When 2,6-dimethylnaphthalene is the aromatic feed compound for the oxidation reaction and a catalyst comprising cobalt, manganese and bromine components is used, the oxidation reaction mixture directly from the oxidation reactor (also called the total reactor effluent or TRE) contains the reaction solvent, which is typically a mixture of acetic acid and water, the desired 2,6-naphthalene dicarboxylic acid, and impurities including trimellitic acid (TMLA), bromo-2,6-naphthalenedicarboxylic acid (Br-2,6-NDA), 2-formyl-6-naphthoic acid (2-FNA), 2-naphthoic acid (2-NA), a collection of other impurities, and cobalt and manganese catalyst components. The acetic acid and water can be removed by evaporation or distillation from the oxidation reaction mixture to leave a residue of solids. Analysis of these solids provides a useful assessment of all of the solid components in the oxidation reaction mixture and consequently an assessment of the yield of desired product and reaction by-products. In a typical oxidation of 2,6-dimethylnaphthalene, the amount of trimellitic acid in the oxidation reaction mixture solids can be as high as 5 weight percent of the solids and typically about 3–4 weight percent. The amount of 2-formyl-6-naphthoic acid can be as high as 1 weight percent and typically is about 0.4–0.5 weight percent. The amount of bromo-2,6-naphthalene dicarboxylic acids can be as high a 3 weight percent and is typically about 0.2 to 1 weight percent. The total of cobalt and manganese in the solid portion of the oxidation reaction mixture can be as high as 4 weight percent. Although the desired 2,6-naphthalene dicarboxylic acid is generally insoluble in the oxidation reaction mixture, particularly when the oxidation reaction mixture is cooled to a temperature below the oxidation reaction temperature, and can be easily separated from the oxidation reaction mixture, the 2,6-naphthalene dicarboxylic acid recovered is also contaminated with trimellitic acid, 2-formyl-6-naphthoic acid, bromo-2,6-naphthalene dicarboxylic acids, other organic impurities and by-products, as well as the cobalt and manganese oxidation metal catalysts. Furthermore, even when the 2,6-naphthalene dicarboxylic acid is separated from the oxidation reaction mixture at an elevated temperature, and even if the separated 2,6-naphthalene-dicarboxylic acid is washed with fresh solvent at an elevated temperature to remove residual mother liquor, the recovered 2,6-naphthalene dicarboxylic acid still contains substantial amounts of the aforementioned impurities by by-products which require removal from the 2,6-naphthalene dicarboxylic acid.

The crude acid produced by the aforesaid liquid-phase oxidation is generally purified by reduction of the impurities therein, for example, by the methods disclosed in the aforesaid U.S. Pat. Nos. 3,584,039; 3,726,915; and 4,405,809. The purification step of the method of the present invention for producing purified terephthalic acid, isophthalic acid, or naphthalene dicarboxylic acid is conducted at an elevated temperature and pressure in a fixed catalyst bed. The crude acid to be purified is dissolved in water or a like polar solvent to form a solution containing from about 5 to about 50 weight percent of the crude acid to be purified. Although water is the preferred solvent, other suitable polar solvents include the relatively lower molecular weight alkyl carboxylic acids containing from 2 to 6 carbon atoms, typically acetic acid, either alone or admixed with water. When the acid to be purified is terephthalic or isophthalic acid, water is the preferred solvent. When the acid to be purified is a naphthalene dicarboxylic acid, a relatively higher purification temperature is employed and a solvent like acetic acid or a mixture of acetic acid and water containing from about 10 to about 90 weight percent of water is the preferred solvent because of its relatively lower vapor pressure. Suitable reactor temperatures for use in this purification step are in the range of from about 100° C. to about 350° C. Preferably, the temperatures employed in the purification step are in the range of about 225° C. to about 300° C.

The pressure employed in the purification step depends primarily upon the temperature employed therein. Inasmuch as the temperatures at which practical amounts of the crude acid being purified may be dissolved in an aforesaid solvent are substantially above the normal boiling point of the solvent, the process pressures are necessarily considerably above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. In general, the reactor pressure during hydrogenation can be in the range of about 200 to abut 1,500 pounds per square inch gauge, and usually is in the range of about 900 to about 1,200 pounds per square inch gauge.

The reactor employed in the purification method of this invention can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the crude acid solution present is the hydrogen partial pressure in the reactor vapor space. Alternatively, if hydrogen is fed in admixture with an inert gas such as nitrogen, the difference between the actual reactor pressure and the vapor pressure of the crude acid solution present is the combined partial pressure of hydrogen and the inert gas admixed therewith. In this case the hydrogen partial pressure can be calculated from the known relative amounts of hydrogen and inert gas present in the admixture. In yet another operating mode, the reactor can be filled with the acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 pounds per square inch gauge to about 200 pounds per square inch gauge, or higher, depending upon the service pressure rating of the reactor, the degree of contamination of the aforesaid crude acid, the activity and age of the particular catalyst employed, and like processing considerations. In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, the amount of hydrogen to be supplied to the purification reactor under reaction conditions is, of course, sufficient to effect the desired hydrogenation.

Catalysts of this invention that are suitable for use in the purification method of this invention are insoluble under the conditions employed therein and comprise at least one supported Group VIII noble metal, whose class includes palladium, rhodium, ruthenium, osmium, iridium, and platinum. The noble metal preferably is at least one of palladium and rhodium and more preferably is palladium. The noble metal component is present on the support at a concentration level in the range of about 0.01 weight percent to about 2 weight percent, based on the total weight of the catalyst, that is, metal plus support, and calculated as the elemental noble metal. Preferably, the catalyst metal loading is about 0.5 weight percent. A typical catalyst of palladium on the support comprises from about 0.01 to about 2 weight percent of palladium, based on the total weight of the catalyst and calculated as elemental metal. The noble metal component can be deposited on the titanium dioxide support by any convenient conventional technique such as spraying or the incipient wetness technique.

The space velocity reported as weight of the crude acid solution per weight of catalyst per hour in the purification step is from about 1 hour$^{-1}$ to about 25 hours$^{-1}$, preferably from about 2 hours$^{-1}$ to about 15 hours$^{-1}$. The residence time of the solution in the catalyst bed varies, depending upon the space velocity.

The support of the catalyst employed in the purification method of the present invention is titanium dioxide support which does not disintegrate in less than one month under the corrosive conditions that prevail in the purification. Such corrosive conditions are an at least partially, and preferably substantially, aqueous solution of from about 5 to about 50 weight percent of the crude acid being purified and a purification temperature of from about 100° C. to about 350° C. The support is formed by an extrusion technique in any convenient form that can be used in a packed bed.

In one preferred embodiment, at least about one weight percent, preferably at least about 90 weight percent, and more preferably 100 weight percent of the titanium dioxide support is in the rutlie crystal phase.

In another preferred embodiment, the titanium dioxide support is formed by calcination of titanium dioxide at a temperature in the range of from about 600° C., preferably from about 800° C., and more preferably from about 900° C., to about 1200° C., preferably to about 1100° C., and more preferably to about 1000° C. In this embodiment, preferably at least 5 weight percent, more preferably at least 70 weight percent, and most preferably substantially 100 weight percent, of the titanium dioxide which is calcined is initially in the anatase crystal phase. In addition, the titanium dioxide being calcined contains preferably from about 0.05, more preferably from about 0.2, and most preferably from about 0.5 weight percent, preferably to about 5, and more preferably to about 3 weight percent of a sulfur-containing component, calculated as elemental sulfur.

In yet another preferred embodiment, the titanium dioxide support contains less than 500 parts per million by weight, preferably less than 100 parts per million by weight of a sulfur-containing component, calculated as elemental sulfur.

In a further preferred embodiment, the titanium dioxide support has a total specific surface area of preferably less than about 40 square meters per gram, more preferably less than about 20 square meters per gram, and most preferably less than about 10 square meters per gram.

In another preferred embodiment, the titanium dioxide support has an average pore diameter of at least about 10 nanometers (nm), preferably at least about 20 nm.

In an especially preferred embodiment, at least one weight percent of the titanium dioxide support is in the rutlie crystal phase whose support contains less than 500 parts per million by weight of a sulfur-containing component, calculated as elemental sulfur, has a total specific surface area of less than about 40 square meters per gram, has an average pore diameter of at least about 10 nm, and is formed by calcination at a temperature of from about 600° C. to about 1200° C. of titanium dioxide of which at least 50 weight percent is in the anatase crystal phase and contains at least one weight percent of a sulfur-containing component, calculated as elemental sulfur.

After hydrogenation, the treated acid solution is separated from the solid catalyst particles. The purified acid is crystallized from the separated solution by cooling it, to a temperature—for example, about 150° C. or below—that is sufficiently low for crystallization of the purified acid to occur but sufficiently high that the impurities and their reduction products remain dissolved in the resulting mother liquor. Thereafter the mother liquor containing the dissolved impurities and their reduction products is separated from the crystallized purified acid, whereby purified crystals of fiber and thin film grade acid are recovered.

The present invention will be more clearly understood from the following specific examples.

EXAMPLE 1

Each of ten two hundred gram samples of titanium dioxide, 100 percent of which was in the anatase crystal phase, was subjected to calcination at a different calcination temperature in the range of 400° C. to 1000° C. for one hour and under a blanket of air and was thereby at least partially converted to the rutlie crystal phase. In each case, the extent of such conversion, the sulfur content, BET surface area, pore volume, pore radius and crush strength of the resulting calcined product were measured, and the results are presented in Table 1. Comparison of these results indicates that as the calcination temperature increases, the extent of conversion to the rutlie crystal phase, pore radius and crush strength increase while the sulfur content, BET surface area, and pore volume decrease.

TABLE 1

| Calcination Temperature (°C.) | Crystal Form Anatase (wt. %) | Crystal Form Rutile (wt. %) | Sulfur Content (ppm wt.) | BET Surface Area (m²/g) | Pore Volume (cc/g) | Pore Radius (nm) | Crush Strength (kg) Fresh/Aged 5 days |
|---|---|---|---|---|---|---|---|
| 400 | 100 | 0 | 6200 | 286 | 0.20 | 14 | 2.3/broke up |
| 500 | 100 | 0 | | | | | 2.3/broke up |
| 600 | 100 | 0 | | | | | 4.5/2.3 |
| 700 | 100 | 0 | | | | | 8.2/2.3 |
| 800 | 99 | 1 | 350 | 12 | 0.15 | 22 | 11.4/5 |
| 850 | 95 | 5 | 130 | 7.2 | 0.11 | 29 | 21.4/8.6 |
| 900 | 55 | 45 | 55 | 5.0 | 0.10 | 33 | 40/31.4 |
| 925 | 9 | 91 | 30 | 3.6 | 0.10 | 50 | 45/45 |
| 950 | 2 | 98 | 20 | 3.2 | 0.10 | 49 | 47.3/39.1 |
| 1000 | 0 | 100 | <10 | 1.7 | 0.09 | 70 | 44.5/36.8 |

EXAMPLES 2-12

The palladium-containing component in Examples 2-12 was deposited on the titanium dioxide support by spraying. In Example 2, a comparison of the properties of a conventional, commercial palladium-on-carbon catalyst with a palladium-on-titanium dioxide catalyst of this invention is presented in Table 2. One hundred percent of the titanium dioxide support was in the ruffle crystal phase and had a sulfur content of 28 parts per million parts by weight, calculated as elemental sulfur. The titanium dioxide support was prepared by calcination at at least 700° C. for one hour under a blanket of air, of titanium dioxide of which 100 weight percent was in the anatase crystal phase and which contained 0.62 weight percent of a sulfur-containing component, calculated as elemental sulfur. The calcined solids were then impregnated with the palladium-containing component as described above. The carbon-supported palladium-containing catalyst was obtained commercially.

Comparison of the results in Table 2 indicates that, although the carbon-supported catalyst has a substantially larger total surface area and pore volume than does the titanium dioxide-supported catalyst, essentially none of the surface area of the carbon-supported catalyst is in pores having radii of at least 40 nm, but essentially all of the surface area of the titanium dioxide-supported catalyst is in pores having radii of at least 40 nm. Similarly, although the pore volume of the titanium dioxide-supported catalyst is smaller than the pore volume of the carbon-supported catalyst, the average pore radius of the titanium dioxide-supported catalyst is substantially larger than that for the carbon-supported catalyst. Thus, the palladium sites on the titanium dioxide-supported catalyst are more readily available than the palladium sites on the carbon-supported catalyst, as indicated by comparison of their palladium surface areas as determined by carbon monoxide adsorption. Furthermore, the titanium dioxide-supported catalyst has a greater crush strength and abrasion resistance than does the carbon-supported catalyst. It is important to recognize that since titania has a bulk density which is substantially larger than the bulk density of carbon, comparisons made on the basis of the use of equal volumes of the two catalysts are more closely indicative of the relative features or performance characteristics in an actual commercial operation.

TABLE 2

| Characteristics | 0.15% Pd/TiO₂ | 0.5% Pd/C |
|---|---|---|
| Total Surface Area | | |
| m²/g | 2.7 | 1000 |
| m²/cc | 4.6 | 450 |
| % Total Surface Area in Pores Having Radii ≧40 nm | ~100 | ~0 |
| Pd Surface Area | | |
| m²/g | 0.15 | 0.42 |
| m²/cc | 0.26 | 0.19 |
| Total Pore volume (cc/g) | 0.13 | 0.33 |
| Average Pore Size (nm) | 80 | 1.5 |
| Crush Strength (kg) | 61 | 3 |
| Loss on Crushing (wt. %) | <0.1 | 1.0 |
| Loss on Abrasion (wt. %) | 0.9 | 4.3 |

In each of Examples 3–10, a sample of the same crude terephthalic acid prepared under the same conditions of elevated temperature and pressure by the liquid phase oxidation with oxygen of p-xylene in acetic acid solution using a cobalt-, manganese-, and bromine-containing oxidation catalyst was purified. In each case, 290 grams of the crude terephthalic acid were dissolved in 1160 grams of water by heating at 276° C. and stirring at 300 revolutions per minute in a one-gallon titanium autoclave. At a reaction temperature of 271° C., hydrogen was introduced into the autoclave to a pressure of 50 pounds per square inch absolute, and then 10 milliliters of the catalyst to be tested, in a 20 mesh titanium wire screen basket through which water could flow freely, were lowered from the vapor phase into the liquid phase to start the purification reaction, and the stirring rate was increased to 1000 revolutions per minute. Liquid samples were withdrawn at various times after the start of the purification reaction and analyzed for the following impurities: 4-carboxybenzaldehyde (4-CBA), 4-hydroxymethyl benzoic acid (4-HMBA), p-toluic acid (PTOL), and benzoic acid (BA). The results are presented in Tables 3 and 4.

In Examples 3–6, the titanium dioxide support employed in this catalyst was the same employed in Example 2, and the palladium-on-titanium dioxide catalyst was also prepared as described in the description of Example 2 and was employed either in Example 3 in the form in which it was thus prepared, as the fresh catalyst, or in Examples 4–6 after having been aged by heating it at 275°–285° C. in admixture with an aqueous solution containing 20–30 weight percent of terephthalic acid in a titanium basket and in the presence of hydrogen. In Examples 7–10, a conventional commercial palladium-on-carbon catalyst was employed either in Example 7 as the fresh catalyst or in Examples 8–10 after having been aged as described above for Examples 4–6. The catalysts employed in Examples 4, 5, 8 and 9 were aged for various periods of time in an autoclave, and the catalysts employed in Examples 6 and 10 were aged in a commercial reactor for the purification of terephthalic acid.

Comparison of the results in Tables 3 and 4 illustrates that, after 2 hours of operation, the titanium dioxide-supported catalyst performed substantially as well as the carbon-supported catalyst in converting 4-CBA and 4-HMBA. Additional results illustrate that, after 6 hours of operation, a titanium dioxide-supported catalyst of this invention that had been aged for 60 days reduced the concentration of 4-CBA and 4-H MBA to substantially lower levels than did a palladium-containing carbon-supported catalyst that had also been aged for 60 days.

taken and analyzed for fines content. Fines were measured as particulates in the size range of 1.1 to 30 microns. The carbon bed produced fines having dimensions up to 30 microns. By contrast, the titanium dioxide bed produced no fines having sizes of 10 microns and above and substantially fewer fines below 10 microns sizes than did the carbon bed.

From the above description, it is apparent that, while only certain embodiments and various modifications will be apparent from the above description to those skilled in the art, these alternatives are considered equivalents and within the spirit and scope of the present invention.

Having described the invention, what is claimed is:

1. A method for the purification of a crude terephthalic acid, crude isophthalic acid or a crude naphthalene dicarboxylic acid produced by the liquid-phase oxidation of benzene having two oxidizable alkyl or

TABLE 3

Concentration (PPM) of Impurities in Solution of Crude Terephthalic Acid Being Purified with 0.5% Pd/TiO$_2$ Catalyst

| | Example 3 Fresh Catalyst | | | | | Example 4 Catalyst Aged in Autoclave for 3 days | | | | |
|---|---|---|---|---|---|---|---|---|---|---|
| Hours | 4-HMBA | 4-CBA | BA | PTOL | Total | 4-HMBA | 4-CBA | BA | PTOL | Total |
| 0 | 84 | 2105 | 756 | 168 | 3114 | 102 | 2123 | 847 | 187 | 3260 |
| 0.5 | 766 | 450 | 1942 | 1231 | 4390 | 823 | 905 | 1126 | 454 | 3309 |
| 1.0 | 482 | 104 | 2815 | 1938 | 5340 | 966 | 345 | 1490 | 803 | 3606 |
| 1.5 | 318 | 42 | 3803 | 2533 | 6697 | 767 | 147 | 1429 | 969 | 3313 |
| 2.0 | 191 | 25 | 4708 | 3004 | 7930 | 636 | 62 | 1757 | 1257 | 3714 |

| | Example 5 Catalyst Aged in Autoclave for 33 days | | | | | Example 6 - Catalyst Aged in Commercial Plant for 60 Days | | | | |
|---|---|---|---|---|---|---|---|---|---|---|
| Hours | 4-HMBA | 4-CBA | BA | PTOL | Total | 4-HMBA | 4-CBA | BA | PTOL | Total |
| 0 | 67 | 2004 | 774 | 169 | 3014 | 115 | 1811 | 667 | 172 | 2765 |
| 0.5 | 665 | 1027 | 1165 | 580 | 3437 | 786 | 915 | 1062 | 462 | 3225 |
| 1.0 | 781 | 474 | 1402 | 801 | 3458 | 804 | 378 | 1173 | 670 | 3025 |
| 1.5 | 718 | 234 | 1675 | 1224 | 3851 | 739 | 192 | 1280 | 859 | 3071 |
| 2.0 | 606 | 119 | 1821 | 1441 | 3987 | 639 | 110 | 1453 | 1038 | 3240 |

TABLE 4

Concentration (PPM) of Impurities in Solution of Crude Terephthalic Acid Being Purified with 0.5% Pd/C Catalyst

| | Example 7 Fresh Catalyst | | | | | Example 8 Catalyst Aged in Autoclave for 3 days | | | | |
|---|---|---|---|---|---|---|---|---|---|---|
| Hours | 4-HMBA | 4-CBA | BA | PTOL | Total | 4-HMBA | 4-CBA | BA | PTOL | Total |
| 0 | 61 | 2340 | ~700 | 199 | 3120 | 168 | 2244 | 1030 | 234 | 3669 |
| 0.5 | 1013 | 218 | 1097 | 1131 | 3459 | 1317 | 337 | 1943 | 725 | 4323 |
| 1.0 | 564 | 70 | 1095 | 1526 | 3255 | 985 | 98 | 1970 | 1015 | 4069 |
| 1.5 | 326 | 48 | 1429 | 1786 | 3589 | 819 | 75 | 2264 | 1360 | 4518 |
| 2.0 | 199 | 43 | 1440 | 2056 | 3738 | 574 | 63 | 2279 | 1496 | 4313 |

| | Example 9 Catalyst Aged in Autoclave for 33 days | | | | | Example 10 - Catalyst Aged in Commercial Plant for 60 Days | | | | |
|---|---|---|---|---|---|---|---|---|---|---|
| Hours | 4-HMBA | 4-CBA | BA | PTOL | Total | 4-HMBA | 4-CBA | BA | PTOL | Total |
| 0 | 132 | 2179 | 1350 | 217 | 3878 | 82 | 1966 | 545 | 188 | 2782 |
| 0.5 | 345 | 2064 | 2319 | 366 | 5094 | 1142 | 743 | 836 | 356 | 3049 |
| 1.0 | 515 | 703 | 2375 | 411 | 5004 | 1355 | 297 | 978 | 536 | 3167 |
| 1.5 | 693 | 1535 | 2643 | 507 | 5378 | 1272 | 164 | 1063 | 668 | 3166 |
| 2.0 | 807 | 1278 | 2753 | 578 | 5416 | 1332 | 120 | 1178 | 844 | 3474 |

Each of Examples 11 and 12 involved laboratory flow experiments to measure the production of fines in a simulation of the purification method of this invention. In each case, a fixed bed of 200 cubic centimeters of either a titanium dioxide support in Example 11 or a carbon support in Example 12 was washed to remove any fines that were initially present and then subjected to a downflow of water at room temperature and atmospheric pressure. After a flow of first 80 and then 160 liters of water per liter of catalyst, samples of water passing down from the bed of catalyst particles were acyl ring substituents or an oxidizable alkyl and acyl ring substituent in the meta or para positions or naphthalene having two oxidizable alkyl or acyl ring substituents or an oxidizable alkyl and acyl ring substituent, with an oxygen-containing gas in a solvent at an elevated temperature and pressure and in the presence of an oxidation catalyst comprising a heavy metal component, wherein the purification comprises passing an at least partially aqueous solution of from about 5 to about 50 weight percent of the crude terephthalic or isophthalic acid or the crude naphthalene dicarboxylic acid, at a temperature of from about 100° C. to about 350° C. and at a pressure sufficient to maintain the solution substantially in the liquid phase, through a particulate catalyst bed and in the presence of hydrogen, wherein the particulate catalyst comprises a noble metal of Group VIII of the Periodic Table of Elements on a titanium dioxide support which does not disintegrate in less than one month under the aforesaid conditions employed in the purification.

2. The method of claim 1 wherein at least one weight percent of the titanium dioxide support is in the rutlie crystal phase.

3. The method of claim 2 wherein at least about 90 weight percent of the titanium support is in the rutlie crystal phase.

4. The method of claim 1 wherein the titanium dioxide support is formed by calcination of titanium dioxide at a temperature in the range of from about 600° C. to about 1200° C.

5. The method of claim 4 wherein calcination is performed at a temperature in the range of from about 800° C. to about 1100° C.

6. The method of claim 5 wherein calcination is performed at a temperature in the range of from about 900° C. to about 1000° C.

7. The method of claim 1 wherein the titanium dioxide support contains less than 500 parts per million by weight of a sulfur-containing component, calculated as elemental sulfur.

8. The method of claim 1 wherein the support has a total specific surface area of less than about 40 square meters per gram.

9. The method of claim 1 wherein the support has an average pore diameter of at least about 10 nm.

10. The method of claim 1 wherein the titanium dioxide support is formed by calcination of titanium dioxide at least 5 weight percent of which is in the anatase crystal phase.

11. The method of claim 1 wherein the titanium dioxide support is formed by calcination of titanium dioxide which contains from about 0.05 to about 5 weight percent of a sulfur-containing component, calculated as elemental sulfur.

12. The method of claim 1 wherein the crude acid being purified is terephthalic acid formed by the oxidation of p-xylene, isophthalic acid formed by the oxidation of m-xytene, or 2,6-naphthalene dicarboxylic acid formed by the oxidation of a 2,6-dialkylnaphthalene.

13. The method of claim 12 wherein the crude acid being purified is terephthalic acid.

14. The method of claim 1 wherein the noble metal of Group VIII is palladium or rhodium.

* * * * *

UNITED STATES PATENT AND TRADEMARK OFFICE
CERTIFICATE OF CORRECTION

PATENT NO.: 5,362,908

DATED: November 8, 1994

INVENTOR(S): Hobe Schroeder, Ricky L. Wittman

It is certified that error appears in the above-identified patent and that said Letters Patent is hereby corrected as shown below:

| Col. | Line | |
|------|------|---|
| 2 | 38 | "the rutlie crystalline phase" should read --the rutile crystalline phase-- |
| 3 | 9 | "zirconlure," should read --zirconium,-- |
| 3 | 11 | "incoriel" should read --inconel-- |
| 3 | 38 | "Timruer et al.," should read --Timmer et al.,-- |
| 5 | 54 | "30 mga per toga of cobalt." should read --30 mga per mga of cobalt.-- |
| 5 | 60-61 | "1.5 mga per toga of total cobalt" should read --1.5 mga per mga of total cobalt-- |
| 6 | 65 | "the toga ratio of manganese to cobalt" should read --the mga ratio of manganese to cobalt-- |
| 6 | 66 | "the toga ratio of bromine" should read --the mga ratio of bromine-- |

UNITED STATES PATENT AND TRADEMARK OFFICE
CERTIFICATE OF CORRECTION

PATENT NO.: 5,362,908

DATED: November 8, 1994

INVENTOR(S): Hobe Schroeder, Ricky L. Wittman

It is certified that error appears in the above-identified patent and that said Letters Patent is hereby corrected as shown below:

Patent reads:

| Col. | Line |   |
|------|------|---|
| 10   | 2    | "the rutlie crystal phase." should read --the rutile crystal phase.-- |
| 10   | 37   | "rutlie crystal phase" should read --rutile crystal phase-- |

Signed and Sealed this

Twenty-eight Day of March, 1995

Attest:

BRUCE LEHMAN

Attesting Officer

Commissioner of Patents and Trademarks